United States Patent
Jeon et al.

(10) Patent No.: US 9,907,759 B2
(45) Date of Patent: Mar. 6, 2018

(54) SILDENAFIL-FREE BASE-CONTAINING FILM PREPARATION AND METHOD FOR PRODUCING SAME

(75) Inventors: Hong-Ryeol Jeon, Suwon-si (KR); Bong-Sang Lee, Suwon-si (KR); Su-Jun Park, Yongin-si (KR); Bong-Geun Cha, Hwaseong-si (KR); Jun-Ki Kim, Chungcheongbuk-do (KR)

(73) Assignee: CTC Bio, Inc., Songpa-gu (KR)

( * ) Notice: Subject to any disclaimer, the term of this patent is extended or adjusted under 35 U.S.C. 154(b) by 386 days.

(21) Appl. No.: 13/984,756

(22) PCT Filed: Feb. 13, 2012

(86) PCT No.: PCT/KR2012/001049
§ 371 (c)(1),
(2), (4) Date: Aug. 9, 2013

(87) PCT Pub. No.: WO2012/108738
PCT Pub. Date: Aug. 16, 2012

(65) Prior Publication Data
US 2013/0323307 A1 Dec. 5, 2013

(30) Foreign Application Priority Data
Feb. 11, 2011 (KR) ........................ 10-2011-0012516

(51) Int. Cl.
| | | |
|---|---|---|
| A61K 9/14 | (2006.01) | |
| A61L 9/04 | (2006.01) | |
| A61K 31/496 | (2006.01) | |
| A61K 9/19 | (2006.01) | |
| A61K 9/20 | (2006.01) | |
| A61K 9/00 | (2006.01) | |
| A61K 9/70 | (2006.01) | |
| A61K 31/519 | (2006.01) | |
| A61K 31/522 | (2006.01) | |

(52) U.S. Cl.
CPC ............ *A61K 9/7007* (2013.01); *A61K 9/006* (2013.01); *A61K 9/0056* (2013.01); *A61K 9/14* (2013.01); *A61K 31/519* (2013.01); *A61K 31/522* (2013.01)

(58) Field of Classification Search
CPC .... A61K 9/2095; A61K 31/522; A61K 9/146; A61K 9/0056
See application file for complete search history.

(56) References Cited

U.S. PATENT DOCUMENTS

| | | | |
|---|---|---|---|
| 4,861,592 A * | 8/1989 | Gottwald | A61K 9/0095 424/686 |
| 6,552,024 B1 * | 4/2003 | Chen et al. | 514/252.16 |
| 2002/0002172 A1 * | 1/2002 | Bell-Huff et al. | 514/258 |
| 2005/0042177 A1 | 2/2005 | Ryde et al. | |
| 2008/0317863 A1 | 12/2008 | Nystrom et al. | |
| 2009/0047330 A1 | 2/2009 | Bangalore | |
| 2010/0173940 A1 | 7/2010 | Leichs et al. | |

FOREIGN PATENT DOCUMENTS

| | | |
|---|---|---|
| CN | 101132769 A | 2/2008 |
| EP | 1752127 A1 | 2/2007 |
| JP | 2003-261439 A | 9/2003 |
| JP | 2004-099510 A | 4/2004 |
| JP | 2005-342154 A | 12/2005 |
| KR | 10-2009-0049883 A | 5/2009 |
| KR | 10-2011-0041412 A | 4/2011 |
| WO | WO 2004/066925 * | 8/2004 |
| WO | 2005/013937 A2 | 2/2005 |
| WO | WO 2007/149276 A2 * | 12/2007 |
| WO | 2010/151020 A2 | 12/2010 |

OTHER PUBLICATIONS

Product Guide—Hydrophilic Matrix Systems (DOW company) obtained online, p. 1 and 8.*
Product Guide—Methocel Cellulose Ethers (DOW company) obtained online, p. 1 and 7.*
International Search Report for PCT Application No. PCT/KR2012/001049 dated Aug. 27, 2012 (3 pages).

* cited by examiner

*Primary Examiner* — Mina Haghighatian
*Assistant Examiner* — Helen Chui
(74) *Attorney, Agent, or Firm* — Nutter McClennen & Fish LLP; John J. Penny, Jr.

(57) ABSTRACT

The present invention provides a method for preparing a film comprising a high amount of a sildenafil free base uniformly dispersed therein and having a suitable thickness and size, as well as flexibility providing good handling stability and being not prone to breaking. The present invention also provides a sildenafil free base-containing film prepared from the method.

14 Claims, No Drawings

SILDENAFIL-FREE BASE-CONTAINING FILM PREPARATION AND METHOD FOR PRODUCING SAME

CROSS-REFERENCE TO RELATED APPLICATIONS

The present application claims priority to Korean Patent Application No. 10-2011-0012516 filed in the Republic of Korea on Feb. 11, 2011, and PCT Application No. PCT/KR2012/001049 filed on Feb. 13, 2012, the disclosures of which are incorporated herein by reference.

TECHNICAL FIELD

The present invention relates to a sildenafil free base-containing film formulation for oral administration and a method for preparing the same.

BACKGROUND

Sildenafil is a representative therapeutic agent among various commercially available agents for treating erectile dysfunction, and it has been commercially available in the form of a tablet formulation containing sildenafil citrate.

When having to use therapeutic agents for erectile dysfunction, in terms of transportability, it is preferable to use film forms, which are often called strips.

However, sildenafil citrate is commercially available in 25, 50 or 100 mg sildenafil citrate-containing tablets, but due to a high single dose, it is not feasible to formulate in a film form. Specifically, the total weight of commercially available film formulations is mostly in the range of 30 to 100 mg, and an active ingredient containing a high dose is difficult to formulate in a film form for the following reasons:

First, in the preparation of a film formulation, a fixed amount of polymer or more must essentially be used to maintain the form of a film. However, in order to load a high amount of an effective ingredient in a limited film size, the amount of such a polymer can only reduce. In the case the amount of polymer is not sufficient, the formed film may not have the desired properties (e.g., flexibility and tension) for handling.

Second, to contain a high amount of active ingredient in a film, the inherent properties of an active ingredient must be overcome. However, if the amount of additives is restricted, it is difficult to offset the inherent properties. Furthermore, if an active ingredient is not dissolved but just dispersed or suspended in the film-making solution, the layer separation of the film-making solution or the non-homogenization of the active ingredient may occur. Such a layer separation or non-homogenization may also occur during preparation of the film-making solution, transportation of the solution for coating, and coating and drying processes.

Third, it is general to increase the viscosity of a solution or suspension for forming a film in the preparation of a film containing a dispersed or suspended active ingredient in a high amount. However, an excessive viscosity may adversely affect the characteristics and quality of a dried film. Accordingly, high viscosity may be a drawback in terms of good production.

SUMMARY

At least at least one embodiment of the present invention is directed to providing a film or strip comprising sildenafil or a pharmaceutically acceptable salt thereof in a high amount and having a thickness and size suitable for administration as well as good handling and superior properties, and a method for preparing the film or strip.

In accordance with one aspect of at least one embodiment of the present invention, there is provided a method for preparing a sildenafil free base-containing film, comprising drying a polymer solution in which a sildenafil free base as an active ingredient is dispersed (substantially not dissolved).

The commercially available sildenafil citrate is not suitable for preparing a film formulation by way of dispersion or suspension because it can dissolve in water and also exhibit a bitter taste in the mouth. Accordingly, the present inventors have endeavored to develop a new form of sildenafil suitable in a film formulation and found that a sildenafil free base is practically insoluble in water, thereby accomplishing the desired object of at least one embodiment of the present invention, and exhibits no taste in the mouth, making the sildenafil free base suitable to be used in a film formulation.

Also, the present inventors have found that when the sildenafil free base is suspended (dispersed) without the substantial dissolution thereof in a polymer solution to form a film, the formed film can still have the desired properties even though the sildenafil free base is used in a high amount.

In the present invention, the term "suspended without the substantial dissolution" means that the sildenafil free base is dissolved in an amount of 15 wt % or less, preferably 10 wt %, more preferably 7 wt %, still more preferably 4 wt %, most preferably 2 wt %, based on the total weight thereof.

In the film formulation according to at least one embodiment of the present invention, the sildenafil free base is not substantially dissolved, which restricts the interaction with a polymer used for forming a film. From this, it is expected that the formed film exhibits the desired properties even though the film comprises a high amount of the sildenafil free base, but the present invention is not limited thereto.

In at least one embodiment of the present invention, the film may be called a strip, orally dissolving film or orally disintegrating film, and refers to a formulation administered by attaching and melting the film on top and below the tongue, oral mucosa and in the mouth. The film formulation according to at least one embodiment of the present invention has an advantage in that it can be administered without water.

Preferably, the sildenafil free base used in the method of at least one embodiment of the present invention has a particle size distribution in which a particle diameter (D10) corresponding to 10% of the distribution is 10 μm or more and a particle diameter (D90) corresponding to 90% of the distribution is 150 μm or less. More preferably, the sildenafil free base has a particle size distribution in which D10 is 8 μm or more and D90 is 100 μm or less, still more preferably a particle size distribution in which D10 is 5 μm or more and D90 is 80 μm or less.

In the method of at least one embodiment of the present invention, the sildenafil free base having a uniform particle size distribution is only used to be stably dispersed and suspended in a film preparation, from which physical stability can be obtained in a film preparation using a low viscosity polymer, thereby improving the processibility of the film. Also, the use of the sildenafil free base having such a particle size distribution in the preparation of the film can provide good characteristics and properties to the film prepared.

For example, if the sildenafil free base used has a particle size distribution exceeding the above-mentioned range, the particles of the sildenafil free base are observed in the film prepared and the film has a rough surface. Also, such a sildenafil free base can easily precipitate during the preparation process, which increases the likelihood of ununiform distribution.

More specifically, when a sildenafil free base having a particle size distribution, wherein D90 is more than 150 µm is used in a film preparation having a low viscosity, particles are visually observed in the film prepared, and the sildenafil free base is precipitated in the film preparation having a viscosity of 4,000 to 8,000 cp within one day, thereby exhibiting poor physical stability.

In order to overcome this problem, i.e., to maintain the suspension stability of the sildenafil free base during the preparation process, it is necessary to increase the viscosity of a film preparation, but the following problems may occur. First, the use of a film preparation having a high viscosity may cause an ununiform coating density in the coating thereof, thereby resulting in the ununiform density (weight) and content of each film unit.

Second, it is difficult to carry out a degassing process which is considered as being essential in the preparation of a film. Third, the use of an additional solvent is inevitably required to overcome the problem due to the high viscosity of the film preparation, however, it may reduce the dispersion stability of the sildenafil free base, and may raise a coating thickness due to an increased amount of solvents, thereby deteriorating the physical stability of the film preparation during a drying procedure after coating. Also, the increase of the coating thickness may cause poor drying results which refers to the generation of cracks or wrinkles on the film prepared.

On the contrary, if the sildenafil free base has a particle size distribution in which D10 is 5 µm or less, the solubility of the sildenafil free base may rapidly increase, which may make it difficult to achieve the object of the at least one embodiment of present invention, that is by way of dispersion or suspension, and the sildenafil free base may agglomerate. Also, the absorption patterns (e.g., $C_{max}$, $T_{max}$) of the sildenafil free base may become unpredictable.

In the method of at least one embodiment of the present invention, it is preferred that a solvent used in the polymer solution comprises water in an amount of 90 wt % or more, preferably 95 wt % or more, more preferably 98 wt % or more thereof so that the sildenafil free base is prevented from being dissolved.

More preferably, at least one embodiment of the present invention provides a method for preparing a sildenafil free base-containing film, comprising dispersing a sildenafil free base in a solution obtained by dissolving a polymer and a plasticizer in a solvent comprising 90 wt % or more of water, and drying the solution to form a dried film, the sildenafil free base having a particle size distribution in which D10 is 5 µm or more and D90 is 80 µm or less, wherein the polymer is used in an amount of 20 to 45 wt %, the plasticizer is used in an amount of 4 to 20 wt %, and the sildenafil free base is used in an amount of 40 to 60 wt %, based on the total weight of the dried film.

In at least one embodiment of the present invention, it is preferred that the polymer used for forming a film has a viscosity of 15 cp or less (preferably 1 to 15 cp) when measured in an aqueous solution containing 2 wt % of the polymer. When the viscosity of the polymer satisfies such a range, the preparation of the film can be easily performed, and the formed film can have the desired properties and can be rapidly disintegrated in the mouth. Examples of the polymer having a viscosity of 15 cp or less include pullulan, low viscosity hydroxypropyl cellulose, low viscosity hydroxypropylmethyl cellulose, etc.

In at least one embodiment of the present invention, in order to increase the strength of the film, a small amount of a polymer having a viscosity of 50 cp or more (preferably 50 to 10,000 cp) when measured in an aqueous solution containing 2 wt % of the polymer may be used together with the above-mentioned polymer having a viscosity of 15 cp or less. In this case, the polymer having a viscosity of 50 cp or more is used in an amount of 20 wt % or less, preferably 10 wt % or less, more preferably 5 wt % or less, most preferably 3 wt % or less, based on the total weight of the film after drying. Examples of the polymer having a viscosity of 50 cp or more include xanthan gum, propylene glycol alginate, sodium alginate, alginic acid, hydroxypropylmethyl cellulose, hydroxypropyl cellulose, guar gum, sodium carboxymethyl cellulose, etc.

The polymer for forming the film which may be used in at least one embodiment of the present invention includes pullulan, hydroxypropyl cellulose, hydroxypropylmethyl cellulose, xanthan gum, sodium alginate, propylene glycol alginate, povidone, poloxamer, polyvinyl alcohol, alginic acid, caraginane, polyethylene oxide, carbomer, calcium carboxymethyl cellulose, sodium carboxymethyl cellulose, gelatin, hydroxyethyl cellulose and a mixture thereof. Among these, pullulan is preferred, and a mixture of pullulan, propylene glycol alginate and xanthan gum is most preferred, in terms of the compatibility with the sildenafil free base used as an active ingredient.

Considering the viscosity and content of the polymer used and the object of at least one embodiment of the present invention, it is preferred that the film preparation has a viscosity of 4,000 to 8,000 cp, more preferably 5,000 to 8,000 cp, most preferably 5,000 to 6,000 cp.

The plasticizer comprised in the film preparation of at least one embodiment of the present invention may be glycerin, sorbitol, polyethylene glycol, propylene glycol, triethyl citrate or a mixture thereof.

Preferably, the film preparation of at least one embodiment of the present invention further comprises a surfactant and/or a dispersing agent. In the method of at least one embodiment of the present invention, the surfactant and/or dispersing agent may be effectively added, thereby more stably dispersing the sildenafil free base between the polymer chain as compared to a simply suspended dispersion solution and ensuring the physical stability of the active ingredient in the film preparation. That is, the surfactant and/or dispersing agent may be used to reduce layer separation and agglomeration between active ingredient particles which are hydrophobic. Each of the surfactant and/or the dispersing agent is preferably used in an amount of 0.1 to 2 wt % based on the total weight of the film preparation.

Examples of the surfactant and/or dispersing agent which may be used in at least one embodiment of the present invention include polysorbates, polyoxyethylene alkyl ethers, polyoxyethylene castor oil, polyoxyethylene stearate, docusate sodium, sodium lauryl sulfate, sorbitan esters and a mixture thereof. Among these, polysorbate 80 is most preferred in terms of the object of the present invention, in particular, the interaction with other components used.

In the film preparation, the solvent is used in an amount of 0.7 to 4 parts by weight, preferably 1.3 to 3.3 parts by weight based on 1 part by weight of the components of the film remained after drying, considering various aspects including the thickness of the film according to the coating of the film preparation, drying speed, and the viscosity of the film preparation.

Further, at least one embodiment of the present invention provides a sildenafil free base-containing film, comprising a sildenafil free base uniformly dispersed in a film comprising pullulan as a polymer, the sildenafil free base having a particle size distribution in which a particle diameter (D10) corresponding to 10% of the distribution is 8 μm or more and a particle diameter (D90) corresponding to 90% of the distribution is 100 μm or less.

Preferably, the sildenafil free base-containing film comprises glycerine as a plasticizer. More preferably, the film further comprises a surfactant (preferably polysorbate 80) and/or a dispersing agent (preferably, docusate sodium).

The sildenafil free base-containing film according to at least on embodiment of the present invention has a thickness of 40 to 200 μm, preferably 60 to 150 μm, more preferably 80 to 120 μm.

In accordance with at least on embodiment of the present invention, provided is a method for preparing a film comprising a high amount of a sildenafil free base uniformly dispersed therein and having a suitable thickness and size, as well as flexibility providing good handling stability and being not prone to breaking. At least one embodiment of the present invention also provides a sildenafil free base-containing film prepared from the method.

DETAILED DESCRIPTION

Hereinafter, various preferred examples of the present invention will be described in detail for better understanding. However, the examples of the present invention may be modified in various ways, and they should not be interpreted as limiting the scope of the invention. The examples of the present invention are just for better understanding of the invention to persons having ordinary skill in the art.

<Measurement of Particle Size and Characteristic Change Depending on the Rpm Variation Of Homogenizer>

A preparative experimentation was conducted to analyze the particle size of a sildenafil free base and the characteristics thereof in several film preparations depending on the rpm conditions (3,000 or 5,000 rpm) of a homogenizer (AGI homomixer) and homogenization times (0, 10 and 30 minutes), the film preparations having the same compositions as the Examples shown in Table 6.

First, the raw materials of a sildenafil free base before homogenization were measured for their particle size using Mastersizer 2000 (Malvern) by a wet method, and the results thereof are shown in Table 1. The same procedure was repeated three times.

TABLE 1

| Formulation | D10 (μm) | D90 (μm) |
|---|---|---|
| 1 (Example 1) | 13.34 | 283.16 |
| 2 (Example 2) | 13.77 | 279.83 |
| 3 (Example 3) | 13.33 | 282.22 |

Particle size variation results after homogenization are shown in Table 2.

TABLE 2

| Conditions | | Particle size (μm) D10 | D90 | Characteristics |
|---|---|---|---|---|
| | Initial | 13.48 | 281.74 | — |
| 3000 rpm | 10 minutes (Example 4) | 10.23 | 115.56 | Particles were visually observed |
| | 30 minutes | 8.91 | 109.66 | Particles were visually observed |
| 5000 rpm | 10 minutes | 8.59 | 85.99 | Particles were scarcely observed visually |
| | 30 minutes (Example 5) | 8.06 | 67.80 | No particle was observed visually |

Meanwhile, in the case that propylene glycol alginate was further added and homogenization was carried out under the same conditions as Example 4, D10 and D90 in particle size distribution were 10.83 μm and 116.34 μm, respectively (Example 6).

<Measurement of Particle Size Change Depending on Homogenization Times>

The particle size changes of a sildenafil free base depending on homogenization times were measured under the condition of a larger scale than the previous experimentation. The homogenization was carried out using a homogenizer (IKA) at 5,000 rpm with increasing homogenization time. The sildenafil free base-containing film preparations used in the homogenization had the same compositions as the Examples shown in Table 6. The measurement results are shown in Table 3.

TABLE 3

| Conditions and Samples | | Particle size (μm) D10 | D90 |
|---|---|---|---|
| Initial | | 13.48 | 281.74 |
| Scale up - 1 (Example 8) | 30 minutes | 8.64 | 82.84 |
| | 60 minutes | 8.34 | 78.21 |
| | 90 minutes | 8.15 | 75.89 |
| | 120 minutes | 7.99 | 71.17 |
| Scale up - 2 (Example 9) | 30 minutes | 8.19 | 79.21 |
| | 60 minutes | 7.96 | 74.23 |
| | 90 minutes | 7.31 | 69.60 |
| | 120 minutes | 7.55 | 68.14 |
| Scale up - 3 (Example 10) | 30 minutes | 8.83 | 83.30 |
| | 60 minutes | 8.35 | 76.49 |
| | 90 minutes | 8.09 | 72.80 |
| | 120 minutes | 7.99 | 71.69 |

<Preparation of Film Having Minimized Particle Size>

In order to prepare films containing sildenafil free base particles having a smaller size, the film preparation having the same compositions as the Example 8 shown in Table 6 were subject to homogenization using a homogenizer (IKA) at 10,000 rpm for 1 hour. The measurement results are shown in Table 4.

TABLE 4

| Conditions | | Particle Size(um) D10 | D50 | D90 | Characteristics |
|---|---|---|---|---|---|
| 10,000 rpm | 30 minutes (Example 11) | 2.18 | 18.79 | 50.41 | No particle was observed. Semitransparent film |
| | 60 minutes (Example 12) | 1.36 | 5.39 | 25.70 | No particle was observed. Semitransparent film Transparency increase as compared to Example 11 |

As shown in Table 4, after homogenization at 10,000 rpm for 30 and 60 minutes, the numerical values of D10/D90 were 2.18/50.41 and 1.36/25.70, respectively, which have significantly decreased as compared to particle sizes obtained after homogenization at 5,000 rpm. Also, as the particle size decreased, the transparency of the finished film increased.

<Evaluation for Property Stability of Film Preparation by Particle Size>

In order to observe whether the film preparations previously obtained caused layer separation thereof or not, and evaluate the characteristics of the film prepared, each sample was taken from the upper part and the lower part of the film preparations to prepare a film, and each unit weight thereof was measured. The results thereof are shown in Table 5.

TABLE 5

| Elapsed Time | Properties | Samples | | Weight Difference Between Upper Part/Lower Part | |
|---|---|---|---|---|---|
| | | Example 4 | Example 10 | Example 4 | Example 10 |
| 1 Day | Layer Separation | No | No | — | — |
| | Characteristics (Film) | Particles were observed on the surface of the film | No particle was observed on the surface of the film | | |
| | Unit Weight | Upper | 99.8 mg | 100.9 mg | 0.3 mg |
| | | Lower | 100.1 mg | 100.4 mg | |
| 3 Days | Layer Separation | No | No | — | — |
| | Characteristics (Film) | Particles were observed on the surface of the film | No particle was observed on the surface of the film | | |
| | Unit Weight | Upper | 97.1 mg | 101.4 mg | 6.5 mg |
| | | Lower | 103.6 mg | 101.2 mg | |
| 7 Days | Layer Separation | No | No | — | — |
| | Characteristics (Film) | Particles were observed on the surface of the film | No particle was observed on the surface of the film | | |
| | Unit Weight | Upper | 93.3 mg | 101.9 mg | 13.5 mg |
| | | Lower | 106.8 mg | 102.2 mg | |

In Table 5, the characteristics refer to those of the film prepared, and the unit weight refers to a weight (mg) per unit area (9.99 cm$^2$) of the film prepared.

The film preparation of Example 4 in which the particle sizes of D10 and D90 were 10.23 μm and 115.56 μm, respectively, exhibited poor stability including layer separation as time passed. For this reason, the ratio of the lower part relative to the upper part in the film preparation increased, thereby leading to an increase in unit weight after drying.

<Preparation of Sildenafil Free Base-Containing Film Formulation>

Film formulations were prepared according to the method and compositions shown in Table 6 as follows.

Examples 11 and 12: A plasticizer, an additive, a sweeting agent, a surfactant and a dispersing agent were added to purified water, followed by dissolving or dispersing by stirring, to which a sildenafil free base was added. Then, homogenization was carried out using a homogenizer (Ultra turrax T-25, IKA) at 10,000 rpm for 30 and 60 minutes, respectively. Thereto, a polymer was added and again homogenized using the same homogenizer to obtain a polymer solution having the sildenafil free base dispersed therein. To the polymer solution, a flavor was added and mixed by stirring. Then, the resulting film preparation was subject to degassing under vacuum at 45° C., cooled to room temperature, and then coated on a PE film in a suitable thickness. The coating was dried at 80° C. to obtain a sildenafil free base-containing film formulation.

Examples 5, 7, 8, 9 and 10: A plasticizer, an additive, a sweeting agent, a surfactant and a dispersing agent were added to purified water, followed by dissolving or dispersing by stirring, to which a sildenafil free base was added. Then, homogenization was carried out using a homogenizer (Ultra turrax T-25, IKA) at 5,000 rpm for 30 minutes. Thereto, a polymer was added and again homogenized using the same homogenizer to obtain a polymer solution having the sildenafil free base dispersed therein. Then, the same procedure of Example 11 was repeated to obtain a sildenafil free base-containing film formulation.

Examples 4 and 6: A plasticizer, an additive, a sweeting agent, a surfactant and a dispersing agent were added to purified water, followed by dissolving or dispersing by stirring, to which a sildenafil free base was added. Then, homogenization was carried out using a homogenizer (Ultra turrax T-25, IKA) at 3,000 rpm for 10 minutes. Thereto, a polymer was added and again homogenized using the same homogenizer to obtain a polymer solution having the sildenafil free base dispersed therein. Then, the same procedure of Example 11 was repeated to obtain a sildenafil free base-containing film formulation.

Examples 1, 2 and 3: A plasticizer, an additive, a sweeting agent, a surfactant and a dispersing agent were added to purified water, followed by dissolving or dispersing by stirring, to which a sildenafil free base was added. Subsequently, the resultant was stirred for a certain time and a polymer was added thereto, followed by stirring again. Then, the same procedure of Example 11 was repeated to obtain a sildenafil free base-containing film formulation.

TABLE 6

| | Ingredients | \multicolumn{12}{c|}{Example (Unit: wt %)} |
| | | 1 | 2 | 3 | 4 | 5 | 6 | 7 | 8 | 9 | 10 | 11 | 12 |
|---|---|---|---|---|---|---|---|---|---|---|---|---|---|
| D10 (um) | | 13.34 | 13.77 | 13.33 | 10.23 | 8.06 | 10.83 | 10.74 | 7.99 | 7.55 | 7.99 | 2.18 | 1.36 |
| D90 (um) | | 283.16 | 279.83 | 282.22 | 115.56 | 67.80 | 116.34 | 69.99 | 71.17 | 68.14 | 71.69 | 50.41 | 25.70 |
| API | Sildenafil | 23.54 | 15.79 | 21.93 | 23.15 | 23.26 | 24.39 | 15.48 | 14.94 | 15.01 | 15.15 | 15.01 | 15.15 |
| Polymer | Pullulan | 7.06 | 3.30 | 5.26 | 6.48 | 6.05 | 6.34 | 9.29 | 9.34 | 9.31 | 9.25 | 9.31 | 9.25 |
| | Propylene glycol alginate | — | 1.26 | 0.88 | — | — | 0.49 | 0.62 | 0.66 | 0.68 | 0.69 | 0.68 | 0.69 |
| | Xanthan gum | 0.04 | 0.08 | 0.07 | 0.07 | 0.05 | 0.04 | 0.06 | 0.06 | 0.02 | 0.01 | 0.02 | 0.01 |
| Plasticizer | Glycerin | 1.88 | 1.26 | 2.19 | 1.39 | 0.47 | 3.42 | 2.79 | 3.88 | 3.10 | 2.01 | 3.10 | 2.01 |
| | Sorbitol | 1.13 | 1.26 | 1.79 | 0.93 | 0.47 | — | — | — | 0.98 | — | 0.98 | — |
| | Polyethylene glycol | — | 0.63 | 1.32 | — | — | — | — | — | 2.05 | — | 2.05 | — |
| | Propylene glycol | — | — | — | 1.39 | 2.79 | — | — | — | — | 3.23 | — | 3.23 |
| Additive | Titanium dioxide | — | 0.05 | — | 0.57 | 0.55 | 0.71 | — | — | — | — | — | — |
| Sweeting agent | Sodium saccharin | 0.04 | 0.03 | 0.04 | 0.05 | 0.05 | 0.06 | 0.05 | 0.06 | 0.06 | 0.07 | 0.06 | 0.07 |
| | Sucralose | 0.04 | 0.03 | 0.04 | 0.05 | 0.05 | 0.06 | 0.05 | 0.06 | 0.06 | 0.06 | 0.06 | 0.06 |
| Surfactant/ Dispersing agent | Polysorbate 80 | 0.04 | 0.05 | 0.07 | 0.35 | 0.35 | 0.37 | 0.46 | 0.27 | 0.30 | 0.40 | 0.30 | 0.40 |
| | Docusate sodium | 0.04 | 0.05 | 0.07 | 0.07 | 0.07 | 0.07 | 0.16 | 0.02 | 0.14 | 0.25 | 0.14 | 0.25 |
| Flavor | | 0.08 | 0.05 | 0.07 | 0.08 | 0.07 | 0.08 | 0.05 | 0.04 | 0.04 | 0.04 | 0.04 | 0.04 |
| Water | | to 100 | to 100 | to 100 | to 100 | to 100 | to 100 | to 100 | to 100 | to 100 | to 100 | to 100 | to 100 |

The film-making solutions and films obtained in Examples 1 to 12 were measured for their properties, and the results thereof are shown in Table 7. The films were evaluated for their tastes and feeling of irritation, and the results thereof are shown in Table 8. For this test, ten subjects were subject to taste each film sample by melting the sample in their mouth for one minute before spitting it out. After testing the taste and strange feeling of one sample, each subject was to rinse their mouth with water. Testing was performed with 30 minute intervals between the samples. The rating for each sample was based on a 1 to 4 scale wherein 1 represents very bad taste or strange feeling; 2, bad taste or strange feeling; 3, moderate taste or strange feeling; and 4, very good taste or strange feeling, and the sum of the scales rated is shown in Table 8.

TABLE 7

| | \multicolumn{6}{c|}{Example} |
| | 1 | 2 | 3 | 4 | 5 | 6 |
|---|---|---|---|---|---|---|
| Viscosity of Film-making solution (cp) | 8500-9000 | 8000-8500 | 8000-8500 | 8000-8500 | 7500-8000 | 8000-8500 |
| Dispersing stability of Film-making solution (1 wk) | Layer separation | Layer separation | Layer separation | Slow particle agglomeration | Good | Layer separation |
| Film Properties | not flexible/ partial agglomeration | wrinkle/rough | not flexible/ partial agglomeration | wrinkle/crack/ rough | wrinkle/crack/ rough | wrinkle/ not flexible/tardy disintegration |
| Result | unacceptable | unacceptable | unacceptable | unacceptable | relatively good | unacceptable |

| | \multicolumn{6}{c|}{Example} |
| | 7 | 8 | 9 | 10 | 11 | 12 |
|---|---|---|---|---|---|---|
| Viscosity of Film-making solution (cp) | 7000-7500 | 5500-6000 | 5000-5500 | 5000-5500 | 5000-5500 | 5000-5500 |
| Dispersing stability of Film-making solution (1 wk) | Good | Good | Good | Good | Good | Good |
| Film Properties | very flexible/ quick disintegration | flexible/ quick disintegration | very flexible/ quick disintegration | very flexible/ quick disintegration | very flexible/ quick disintegration | very flexible/ quick disintegration |
| Result | very good | very good | very good | very good | very good | very good |

TABLE 8

| Test | Example |  |  |  |  |  |  |  |  |  |  |  |
|---|---|---|---|---|---|---|---|---|---|---|---|---|
|  | 1 | 2 | 3 | 4 | 5 | 6 | 7 | 8 | 9 | 10 | 11 | 12 |
| Taste | 40 | 40 | 40 | 40 | 40 | 40 | 40 | 40 | 40 | 40 | 13 | 11 |
| Feeling of irritation | 12 | 12 | 11 | 25 | 40 | 22 | 40 | 40 | 40 | 40 | 40 | 40 |

As shown in Table 7, the film-making solutions having similar particle size of Examples 5, 7, 8, 9 and 10 not only exhibited a low viscosity but also good dispersing stability of the sildenafil free base particles which were dispersed but not dissolved, as well as flexibility providing good handling stability and were not prone to breaking, and also were suitable to oral administration due to the fast melting thereof. Furthermore, as shown in Table 8, the film preparations having similar particle size of Examples 5, 7, 8, 9 and 10 were subject to very favorable evaluation in the taste and irriration-feeling test in the mouth.

What is claimed is:

1. A method for preparing a sildenafil free base-containing film, comprising:
    drying a polymer solution in which a sildenafil free base as an active ingredient is dispersed, wherein the sildenafil free base has a particle size distribution in which a particle diameter (D10) corresponding to 10% of the distribution is about 8 μm to about 10 μm and a particle diameter (D90) corresponding to 90% of the distribution is about 67 μm to 100 μm.

2. The method according to claim 1, wherein a solvent used in the polymer solution comprises water in an amount of 90 wt % or more relative to the weight of the polymer solution or more thereof so that the sildenafil free base is prevented from being dissolved.

3. The method according to claim 2, wherein the solvent used in the polymer solution comprises water in an amount of 95 wt % or more relative to the weight of the polymer solution or more thereof so that the sildenafil free base is prevented from being dissolved.

4. A method for preparing a sildenafil free base-containing film, comprising:
    dispersing a sildenafil free base in a solution obtained by dissolving a polymer and a plasticizer in a solvent comprising 90 wt % or more of water, and drying the solution to form a dried film, the sildenafil free base having a particle size distribution in which D10 is about 8 μm to about 10 μm and D90 is about 67 μm to 100 μm, wherein the polymer is used in an amount of 20 to 45 wt %, the plasticizer is used in an amount of 4 to 20 wt %, and the sildenafil free base is used in an amount of 40 to 60 wt %, based on the total weight of the dried film.

5. The method according to claim 1, wherein the polymer has a viscosity of 15 cp or less when measured in an aqueous solution containing 2 wt % of the polymer.

6. The method according to claim 5, wherein the polymer is a mixture of a polymer having a viscosity of 15 cp or less and a polymer having a viscosity of 50 cp or more, each viscosity being measured in an aqueous solution containing 2 wt % of each polymer.

7. The method according to claim 6, wherein the polymer comprises pullulan, propylene glycol alginate and xanthan gum.

8. The method according to claim 1, wherein the solution further comprises a surfactant, a dispersing agent, or a mixture thereof.

9. The method according to claim 1, wherein the polymer comprises pullulan.

10. The method according to claim 1, wherein the polymer solution comprises a solvent used in an amount of 1.3 to 3.3 parts by weight based on 1 part by weight of the components of the film remained after drying.

11. A sildenafil free base-containing film, comprising a sildenafil free base uniformly dispersed in a film comprising pullulan as a polymer, the sildenafil free base having a particle size distribution in which a particle diameter (D10) corresponding to 10% of the distribution is 8 μm to about 10 μm and a particle diameter (D90) corresponding to 90% of the distribution is about 67 μm to 100 μm.

12. The sildenafil free base-containing film according to claim 11, which comprises glycerine as a plasticizer.

13. The sildenafil free base-containing film according to claim 12, which further comprises a surfactant, a dispersing agent, or a mixture thereof.

14. The sildenafil free base-containing film according to claim 11, wherein the polymer further comprises pullulan, propylene glycol alginate and xanthan gum.

* * * * *